United States Patent [19]

Nordlander et al.

[11] Patent Number: 5,078,153
[45] Date of Patent: Jan. 7, 1992

[54] METHOD AND APPARATUS FOR SENSING AND TREATING BRUXISM

[75] Inventors: Jeffrey Y. Nordlander, 1020 40th St., Sacramento, Calif. 95819; Louis J. Gallia, 2259 Swarthmore St., Sacramento, Calif. 95825; Dennis A. Burman, 449 Curie Dr., San Jose, Calif. 95123

[73] Assignees: Jeffrey Y. Nordlander; Louis J. Gallia, both of Sacramento, Calif.

[21] Appl. No.: 584,375

[22] Filed: Sep. 17, 1990

Related U.S. Application Data

[63] Continuation of Ser. No. 324,110, Mar. 16, 1989, abandoned.

[51] Int. Cl.$^5$ .............................................. A61B 5/103
[52] U.S. Cl. .................................... 128/777; 128/782; 433/215; 340/573
[58] Field of Search ............... 128/774, 776, 777, 782, 128/787, 905; 340/573, 575; 433/6, 167, 215, 68, 69; 606/234, 235

[56] References Cited

U.S. PATENT DOCUMENTS

| | | | |
|---|---|---|---|
| 3,983,865 | 10/1976 | Shepard . | |
| 4,169,473 | 10/1979 | Samelson | 128/136 |
| 4,220,142 | 9/1980 | Rosen | 340/575 |
| 4,304,227 | 12/1981 | Samelson | 128/848 |
| 4,355,645 | 10/1982 | Mitani et al. | 128/777 |
| 4,629,424 | 12/1986 | Lauks | 128/777 |
| 4,631,477 | 12/1986 | Nickel et al. | 128/777 |
| 4,669,477 | 6/1987 | Ober | 128/777 |
| 4,842,519 | 6/1989 | Dworkin | 128/777 |

Primary Examiner—Randy Citrin Shay
Attorney, Agent, or Firm—Kelly, Bauersfeld & Lowry

[57] ABSTRACT

An intraoral acrylic splint having incorporated into the interior of the splint a strip of piezoelectric film which emits a small electrical current when deformed by the compression of the teeth. The piezoelectric film is connected by conductors to a small battery powered radio transmitter contained in the splint. The transmitter generates and broadcasts a radio frequency signal when current is received from the piezoelectric film. The radio frequency signal is received by a remote receiver unit. The receiver unit emits an audible alarm upon receiving a signal from the radio transmitter of the splint. The audible alarm alerts the patient of his action, allowing him to consciously resist bruxing.

9 Claims, 4 Drawing Sheets

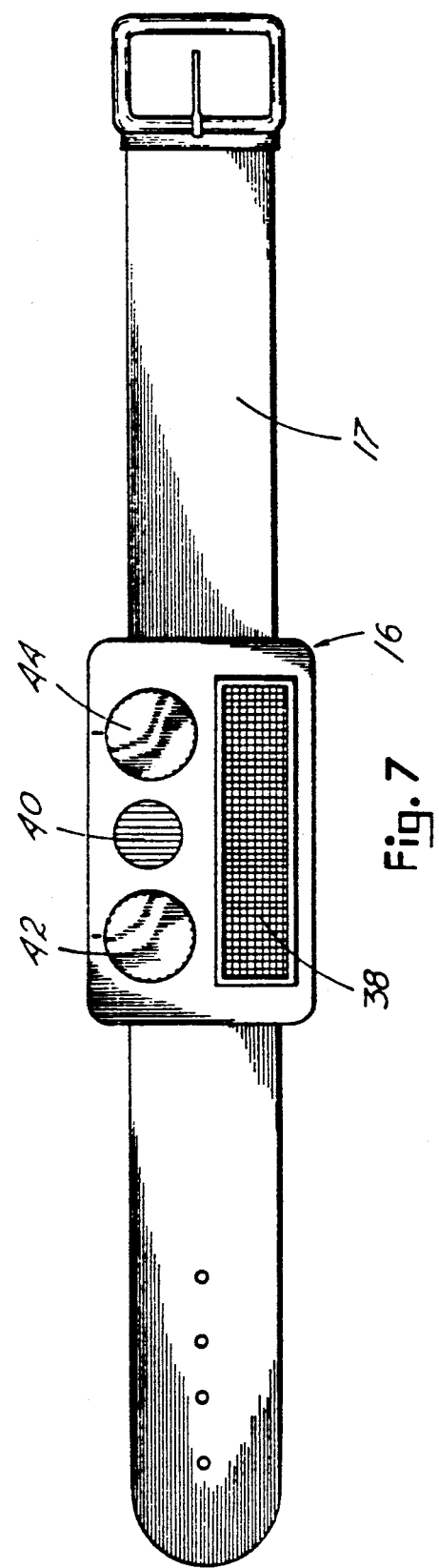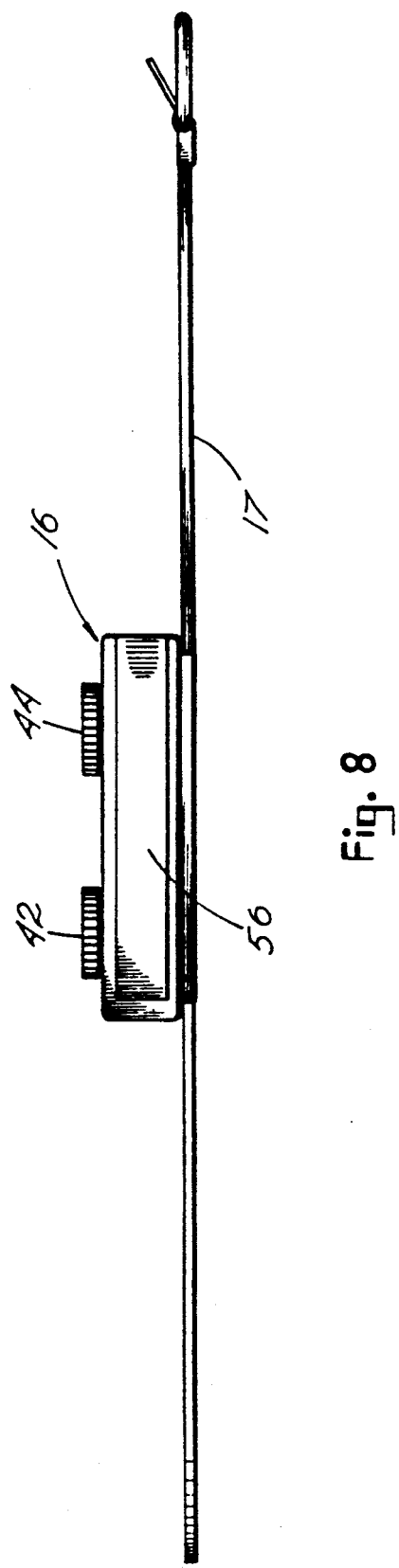

METHOD AND APPARATUS FOR SENSING AND TREATING BRUXISM

This is a continuation of copending application Ser. No. 07/324,110 filed on Mar. 6, 1989, now abandoned.

BACKGROUND OF THE INVENTION

1. Field of the Invention:

This invention relates to methods and devices used to detect and control bruxism.

2. Description of the Prior Art:

The habit of a person grinding his teeth is especially difficult to treat since the action occurs most often when the person is asleep and unaware of the occurrence. This habit may be so unconscious it can also occur during waking hours without the person being aware of it. If left untreated, the habit may lead to permanent deterioration of the teeth, displacement of internal temporomandibular structures, and pain during mastication.

A major cause of bruxing appears to be emotional or psychological stress which triggers an innate physiologic response of clenching or grinding the teeth. The nocturnal occurrence and unconsciousness of the response make the problem extremely difficult to treat. Awareness of each episode of bruxism can enable the person to gain control of the activity and thereby reduce or eliminate the symptoms.

The known prior art which appears to be most relevant to my invention includes devices involving electrical neuromuscular stimulators designed to physically open the jaw muscle during a bruxing episode. Other known past art inventions consist of intraoral ambient sensing devices which monitor a variety of functions such as chewing pressure, specific chemical analysis within the mouth and temperature variations. Still other known past art devices are oral splints designed to simply maintain separation between the teeth.

None of the known past art devices and methods appear to be as effective in sensing and treating bruxism as my invention. This is mainly due to the level of convenience to the patient of my invention over those of the past art. The known past art methods and devices operate in such a way that speech would be difficult or impossible while wearing the device, making the units inconvenient to wear during work. A bruxing sensor and treatment method truly functional for day time use must be capable of being worn on the body with the patient not significantly restricted in movement, speech, or other forms of normal daily activities.

SUMMARY OF THE INVENTION

In utilizing my invention, I have developed a new and convenient method of accurately sensing and recording the occurrence of bruxing, and treating the condition through the use by biofeedback. Through the use of an audible alarm activated by a pressure sensitive splint in the patient's month, the patient is made aware of his bruxing activities and can learn to control the condition at the conscious level. Once the ability to consciously control bruxism has been learned by the patient, treatment may be terminated.

The splint used in my system is constructed of a pliable resilient acrylic plastic from a custom plaster cast of the patient's teeth and thus is comfortable and fairly non-restrictive to a person's speech. Splint appliances are well known in the field of dentistry, and many of the currently known fabrication techniques and materials will apply to my mouthpiece. My splint includes the addition of a thin layer of piezoelectric sensing material connected to a miniaturized battery powered radio transmitter, both of which are held within the material of the splint. The piezoelectric sensing material is encapsulated within the resilient material in the splint, positioned directly over the teeth when in use. The piezoelectric sensing material emits electrical current when pressure is applied or when deformation occurs due to grinding of the patient's teeth. The amount of electrical current generated is proportional to the degree of pressure or deformation. This electrical current is carried by conductors to the miniaturized radio transmitter located in the splint. A signal inaudible to the human hear is then transmitted from the miniaturized transmitter to a separate remote portable receiver unit.

The receiver unit includes an amplifier which when activated produces an audible tone or alarm to alert the patient to his bruxing. Upon hearing the alarm the patient stops grinding his teeth. Over an extended period of treatment the patient learns to control his habit, reducing or eliminating the occurrences of bruxing and the need for treatment.

The remote receiver unit is available in three embodiments. One embodiment includes inaudible signal receive, audible tone transmission, and data record capabilities. This embodiment is a remote battery powered pocket pager sized unit with computerized memory and a data display screen.

The second embodiment of remote receiver is an earpiece unit similar in appearance and use to a hearing-aid. This second embodiment can receive inaudible signal transmissions and emit an audible tone, but does not have the data record and display capabilities of the first embodiment.

The third embodiment of remote receiver is provided in a wristwatch style unit having the same capacity as the earpiece unit. All the necessary elements are included in a housing which is affixed to an adjustable strap.

The triggering of the audible alarm of the receiver unit, based on the inaudible signal from the transmitter in the splint is adjustable by way of a threshold control knob on each receiver embodiment. Low pressure bruxing episodes can be calibrated below the threshold, thus eliminating the activation of the alarm for inconsequential stimuli.

Therefore, it is a primary object of my invention to provide a method of sensing bruxism which activates an audible alarm when bruxing occurs, for the purpose of alerting the patient to his action, thereby allowing the patient to consciously work towards effecting long term behavioral modification.

Another object of my invention is to incorporate a method of recording data on the bruxing episodes for later examination and analysis.

A further object of my invention is to provide a bruxing sensor which may be comfortably used while asleep and may also be conveniently used while performing daily activities without significant interference with the normal behavior or appearance of the wearer.

Further objects and advantages of my invention will be better understood with a reading of the remaining specification and a subsequent comparison of the numbered parts described therein with the similarly numbered parts shown in the accompanying drawings.

DESCRIPTION OF THE DRAWINGS

FIG. 7 is a top view of the third embodiment or wristband receiver transmitter unit.

FIG. 8 is a side view of the wristband receiver transmitter.

DESCRIPTION OF THE PREFERRED EMBODIMENTS

Figure 1:
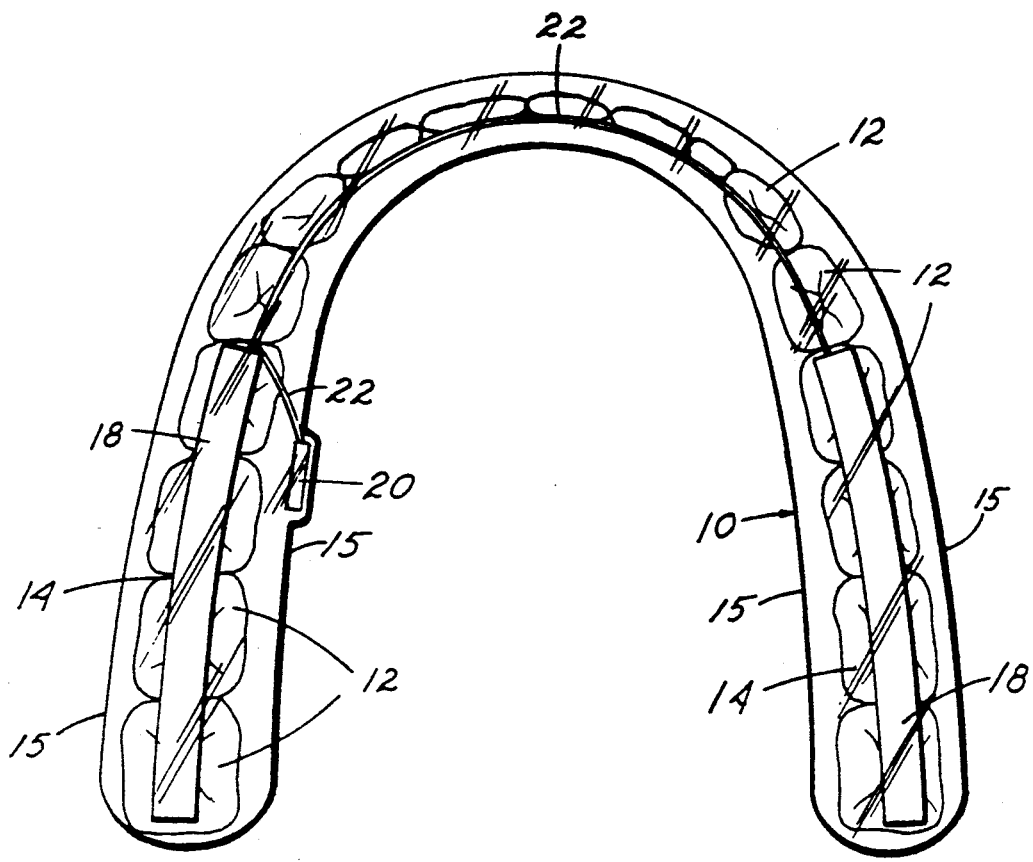
FIG. 1 is a top plan view of the splint positioned over the teeth of a patient.

Referring now to the drawings where the various components of the invention are illustrated. Splint 10 is structured of a non-toxic resilient acrylic polymer which is formed from a plaster cast of the patient's teeth 12 using basic fabrication techniques well known to those skilled in the art. Splint 10 forms a three sided ridge having sidewalls 15 on the sides of teeth 12, and a top surface 14 covering the occlusal portion of teeth 12. Impressions of the bite surface of the opposing teeth 12 are molded into the exterior top surface 14 of splint 10 for additional user comfort. Splint 10 can be structured to be worn on either the upper or lower teeth 12.

The section of splint 10 adjacent front teeth 12 is designated as the front with the remaining sides designated as the right and left sides respectively. Splint 10 can be manufactured in laminated layers or molded in one piece. Top surface 14 in either case is molded thin allowing the area to be very flexible and resilient.

A layer of pressure sensitive material, piezoelectric film 18, is encapsulated in the material of top surface 14 of splint 10. Normally, piezoelectric film 18 is positioned over the last four molars on each side splint 10 as shown in FIG. 1 where two strips of film 18 is used. Splint 10 can also be structured into a much smaller partial mouthpiece sized for application to only one or two teeth 12. Piezoelectric film 18 generates a small amount of electrical voltage when pressure is applied or when deformed by pressure from the upper teeth grinding against the lower teeth. The amount of voltage generated by film 18 is proportional to the degree of compression or deformation. Both sections of piezoelectric film 18 are connected to a self-contained miniaturized battery operated radio signal transmitter 20 by conductors 22. Both radio transmitter 20 and conductors 22 are encapsulated within the material of splint 10. Transmitter 20 is positioned along one interior sidewall 15 of splint 10 near the lingual of bicuspid teeth 12 as shown in FIG. 1.

Figure 2:
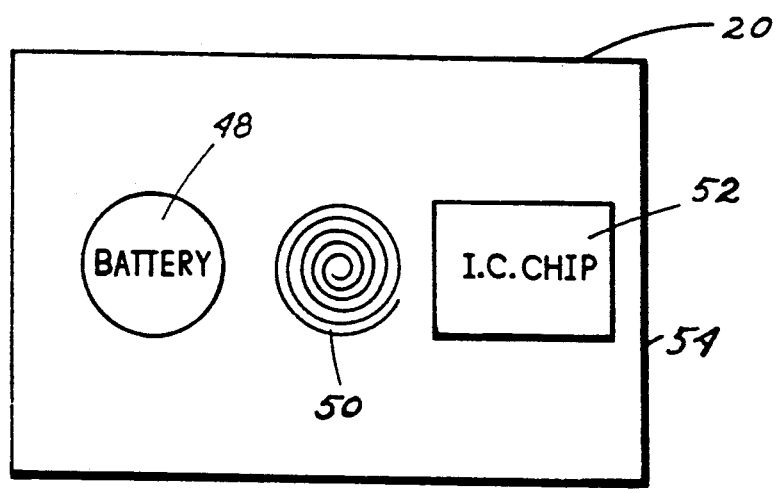
FIG. 2 is an illustrative view showing the basic components of the miniature radio transmitter of the splint.
Figure 3:
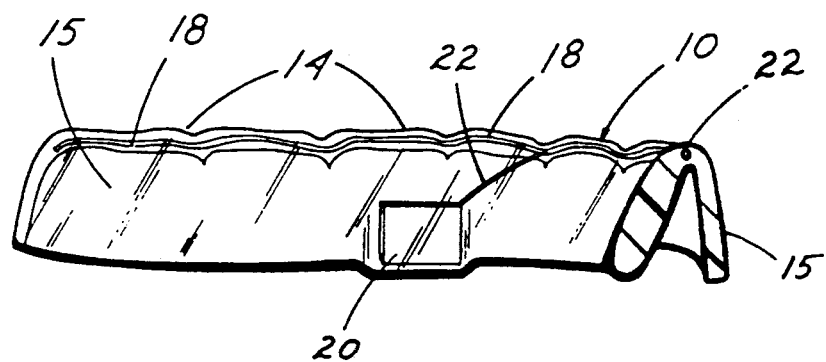
FIG. 3 is a sectional side view of the splint.
Figure 4:
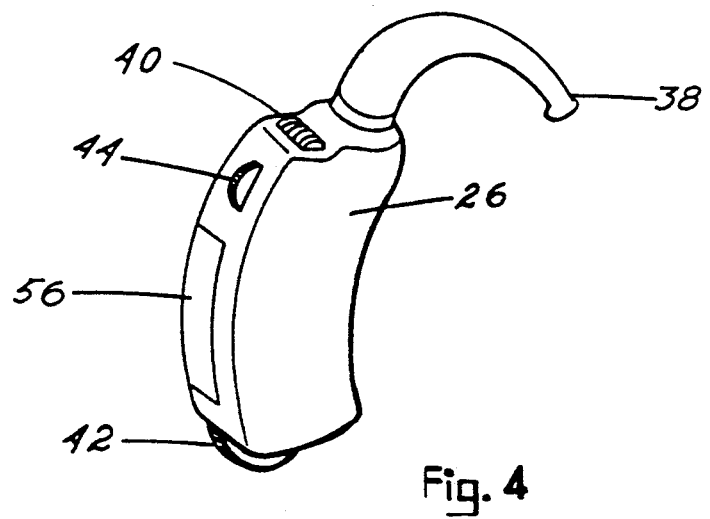
FIG. 4 is a perspective view of the earpiece receiver transmitter unit.
Figure 5:
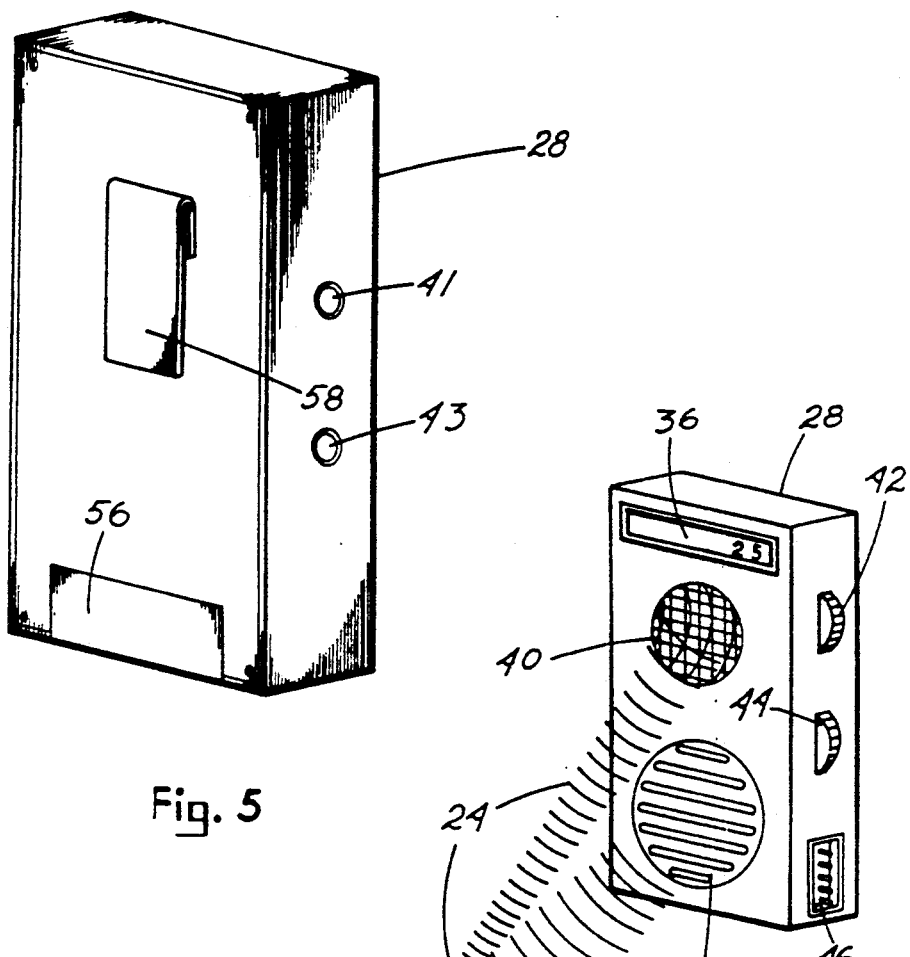
FIG. 5 is a perspective view of the back of the pocket receiver transmitter.
Figure 6:
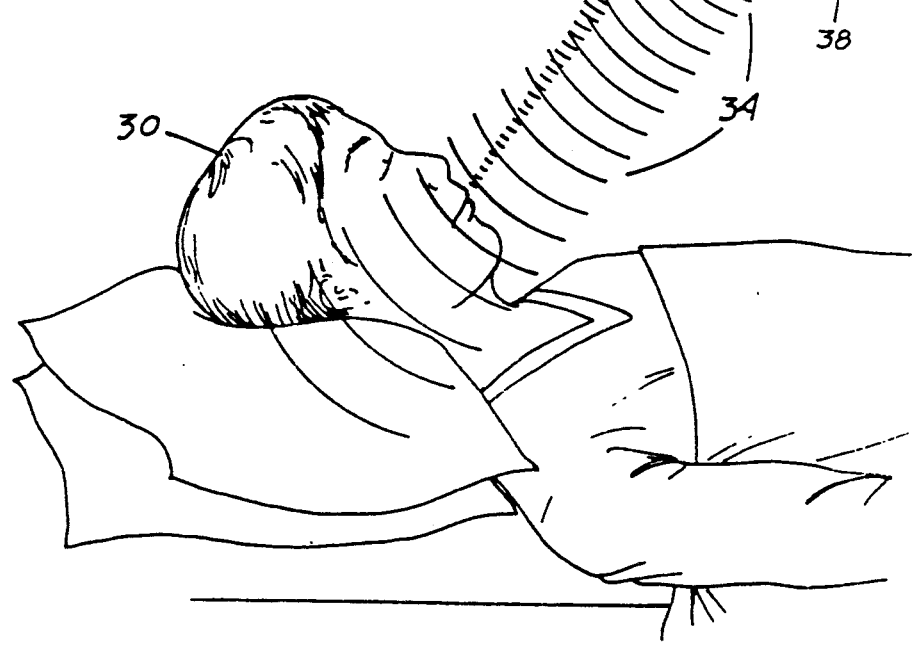
FIG. 6 illustrates a sleeping patient wearing the splint. Inaudible radio transmissions broadcast from the patient's mouth are shown striking the remote pocket receiver transmitter and recorder unit. The remote receiver transmitter is shown broadcasting an audible tone toward the patient to alert him of his bruxing.

In FIG. 2 the major components of signal transmitter 20 are illustrated. Shown is battery 48 for powering inaudible signal transmissions 24, an etched antenna 50 for broadcasting transmissions 24, and an integrated circuit chip 52 for processing the triggering electrical current received from piezoelectric film 18 and generating inaudible radio signal 24 to be broadcast by way of antenna 50. The major components are all held within a sealed housing 54.

Signal transmitter 20 using power from battery 48, when initiated by triggering electrical current from piezoelectric film 18 transmits the inaudible signal 24 in a form proportionally representative of the amount of current received from piezoelectric film 18. Inaudible signal 24 is received by one of three embodiments of remote receiver transmitter units; either earpiece receiver transmitter 26, pocket receiver transmitter 28 or wristband receiver transmitter 16, depending on which receiver is selected for use. Earpiece receiver transmitter 26, is worn on the patient's 30 ear similar to a hearing aid and is normally used when an audible tone broadcast throughout the room would not be acceptable to others. Pocket receiver transmitter 28 is structured as a small rectangular pocket-sized unit and is available with a spring clip 58 on the backside of the unit to allow securing to a belt or in a shirt pocket if desired. Pocket receiver transmitter 28 is designed to compile specific information which will be further explained later in the disclosure. Wristband receiver transmitter 16 consists of the basic elements found in earpiece receiver transmitter 26 housed within a plastic casing mounted on an adjustable strap 17, as seen in FIG. 7 and 8. Wristband receiver 16 is designed to be worn on the patient 30 wrist secured by adjustable strap 17.

Remote receiver transmitter units 16, 26 and 28 are self-contained battery powered units having receiver transducers 40 for receiving inaudible signal 24 from signal transmitter 20. From receiver transducer 40, inaudible signal 24 is circuited to internal processing circuitry. The internal processing circuitry in each receiver transmitter possesses an adjustable threshold level which when exceeded activates additional circuitry containing tone generating and amplification capabilities powered by the internally held replaceable batteries. When the tone generating and amplification circuitry is activated, the generated signal is circuited to a speaker 38 for broadcasting the signal as an audible alarm 34 or tone. The volume of audible alarm 34 is in direct relationship to the degree of pressure applied to piezoelectric film 18 and will range from low to high volume depending on the magnitude of the pressure applied to film 18. Speaker 38 is located on the front of receiver transmitter 16 and 28, and on the ear side of earpiece receiver transmitter 26.

Receiver transmitter units 16, 26 and 28 all have a manually operable power on/off volume control knob 42 for switching the power off and for controlling the volume range of audible alarm 34. Each receiver transmitter unit has a manually operable threshold control knob 44 for adjusting the threshold level at which inaudible signal 24 activates the tone generating and amplification circuitry. Under normal use the threshold would be set at a level which would at least allow the patient to close his mouth with his teeth together in the normal manner without setting off the alarm. The batteries of receiver units 16, 26, and 28 are replaceable by way of a removable battery housing cover 56 on each unit.

The internal circuitry of pocket receiver transmitter 28 additionally contains circuitry for electronically recording the duration, the number of occurrences, and the time at which each episode of bruxism occurs above the threshold level. On the front of pocket receiver transmitter 28 is a small display screen 36 which displays the number of threshold exceeding events which have occurred. Screen 36 displays by way of light emitting diodes or other suitable means. On the side of pocket receiver transmitter 28 is recorded data output jack 46 for removable cable connection to an additional external data processing instrument such as a computer. Positioned on one side of receiver transmitter 28 is a push button recorded data down load switch 41 and a clear memory switch 43. Through output jack 46, the recorded data can be down loaded by activating down load switch 41 into more sophisticated data processing equipment where it can be compiled and analyzed. The stored data in the memory of receiver transmitter 28 can then be cleared by pressing the clear memory switch 43.

In use, splint 10 is inserted into the mouth of patient 30. Earpiece receiver transmitter 26 is attached to the ear, wristband unit 16 is strapped to the wrist, or pocket receiver transmitter 28 is selected for use. When the upper and lower teeth 12 compress sufficiently to deform piezoelectric film 18, inaudible signal 24 is transmitted to the remote receiver transmitter in use. If inaudible signal 24 is sufficient to exceed the set threshold, the remote receiver transmitter emits an audible alarm 34 which wakes patient 30 from sleep, or alerts him to his unconscious action if he is awake. When using pocket receiver transmitter 28, inaudible signal 24 which exceeds the set threshold level not only causes activation of audible alarm 34 to alert patient 30, but compiles information concerning the frequency, duration and time of the bruxing episodes. When utilizing wristband receiver transmitter 16, the action and effect are the same as that of earpiece receiver transmitter 26 although audible alarm 34 is increased due to the additional distance from the ear of wristband 16.

This type of biofeedback application allows patient 30 to become aware of his actions and therefore instigate a change in his behavior. This method is especially effective when the device can be used at home and during normal daily routine at the actual moment the episode occurs.

Although no specific circuitry or electronic components have been described in great detail, those skilled in the art will recognize that the actual circuitry needed for operation of my invention is well known, and can be accomplished with a variety of well known circuits, integrated circuit chips, and individual electronic components.

I have described my invention with considerable details in the specification, however, it is obvious that a person skilled in the art will be able to make modifications after reading this disclosure. Therefore, I will consider these modifications made to the method and structure as my invention when those modifications fall within the intended scope of my appended claims.

What I claim as my invention is:

1. A method for sensing and treating bruxism comprising the steps of:

(a) sensing pressure between upper and lower teeth by use of pressure sensitive material encapsulated within one surface of an intraoral splint, said surface of the splint positioned between the upper and lower teeth;
   (b) converting the sensed pressure to electrical current in proportion to the level of sensed pressure;
   (c) transmitting the electrical current as an inaudible radio signal by transmitter means encapsulated within said intraoral splint;
   (d) receiving the inaudible signal with receiver means; and
   (e) amplifying said inaudible signal to an audible alarm when the signal represents a pressure level exceeding a predetermined threshold.

2. The method for sensing and treating bruxism of claim 1 wherein said pressure sensitive material is piezoelectric material.

3. The method for sensing and treating bruxism of claim 1 wherein a miniaturized battery encapsulated within said intraoral splint provides electrical power for transmitting the electrical current.

4. The method for sensing and treating bruxism of claim 1 further including the step of recording pressure data represented by said inaudible signal.

5. An apparatus for sensing and treating bruxism comprising:

(a) an intraoral splint sized and shaped to fit in a human mouth with one surface thereof positioned between the upper and lower teeth;
   (b) means for sensing pressure between the upper and lower teeth, said means encapsulated within said one surface of said intraoral splint, said sensing means converting said sensed pressure to electrical current in proportion to the level of sensed pressure;
   (c) means for transmitting the electrical current as an inaudible signal, said transmitting means encapsulated within said intraoral splint; and
   (d) means for receiving said inaudible signal and, when said inaudible signal represents a pressure level exceeding a predetermined threshold level, amplifying said inaudible signal to provide an audible alarm.

6. The apparatus for sensing and treating bruxism of claim 5 wherein said pressure sensing means comprises piezoelectric material.

7. The apparatus for sensing and treating bruxism of claim 5 wherein said transmitting means is powered by at least one miniaturized battery encapsulated within said intraoral splint.

8. The apparatus for sensing and treating bruxism of claim 5 wherein said audible alarm has a volume proportional to the level of sensed pressure.

9. The apparatus for sensing and treating bruxism of claim 5 further including means for recording pressure data represented by said inaudible signal.

* * * * *